(12) United States Patent
Van Dijk et al.

(10) Patent No.: US 8,421,000 B2
(45) Date of Patent: Apr. 16, 2013

(54) BEAM SHAPING WITHOUT INTRODUCING DIVERGENCE WITHIN A LIGHT BEAM

(75) Inventors: Erik Martinus Hubertus Petrus Van Dijk, Eindhoven (NL); Sjoerd Stallinga, Eindhoven (NL); Dirk Leo Joep Vossen, Eindhoven (NL); Marius Iosif Boamfa, Eindhoven (NL)

(73) Assignee: Koninklijke Philips Electronics N.V., Eindhoven (NL)

( * ) Notice: Subject to any disclaimer, the term of this patent is extended or adjusted under 35 U.S.C. 154(b) by 396 days.

(21) Appl. No.: 12/743,024

(22) PCT Filed: Nov. 20, 2008

(86) PCT No.: PCT/IB2008/054881
§ 371 (c)(1),
(2), (4) Date: May 14, 2010

(87) PCT Pub. No.: WO2009/066261
PCT Pub. Date: May 28, 2009

(65) Prior Publication Data
US 2010/0264295 A1    Oct. 21, 2010

(30) Foreign Application Priority Data

Nov. 23, 2007    (EP) .................................. 07121417

(51) Int. Cl.
*G02F 1/01*    (2006.01)
*G02B 5/30*    (2006.01)

(52) U.S. Cl.
USPC ...................................... 250/225; 359/489.07

(58) Field of Classification Search ............... 250/201.1, 250/201.5, 225; 359/489.01, 489.07, 489.11, 359/489.12
See application file for complete search history.

(56) References Cited

U.S. PATENT DOCUMENTS

| 4,079,247 | A | 3/1978 | Bricot et al. |
| 6,278,548 | B1 | 8/2001 | Shimano et al. |
| 2001/0030290 | A1 | 10/2001 | Stern |
| 2005/0274870 | A1 * | 12/2005 | Katayama .................. 250/201.5 |
| 2006/0209643 | A1 * | 9/2006 | Schleipen .................. 369/44.23 |

* cited by examiner

*Primary Examiner* — Thanh Luu

(57) ABSTRACT

An optical beam shaper comprises a polarization-dependent phase adjustment member which applies a phase pattern of equal magnitude and opposite sign to two orthogonal polarization states. In a preferred embodiment the beamer shaper is a dif tractive element made of a birefringent material, such as a photo-polymerizable liquid crystal polymer frozen in a uniaxial alignment, said dif tractive element comprising a plurality of zones, each zone having a stepped thickness defining a plurality of steps. The beam shaper can be used to introduce astigmatism to a polarized light beam or to undo the astigmatism to a beam with an orthogonal polarization state. The beam shaper is advantageously used within a detection device, such as a fluorescence scanner.

8 Claims, 4 Drawing Sheets

| subzone | x [mm] | rho | phase [2π] | subzone | x [mm] | rho | phase [2π] |
|---|---|---|---|---|---|---|---|
| 1 | 0 | 0 | 0 | 46 | 1.301182 | 0.743532 | 11.25 |
| 2 | 0.193969 | 0.110839 | 0.25 | 47 | 1.31556 | 0.751748 | 11.5 |
| 3 | 0.274313 | 0.15675 | 0.5 | 48 | 1.329783 | 0.759876 | 11.75 |
| 4 | 0.335964 | 0.191979 | 0.75 | 49 | 1.343855 | 0.767917 | 12 |
| 5 | 0.387937 | 0.221679 | 1 | 50 | 1.357781 | 0.775875 | 12.25 |
| 6 | 0.433727 | 0.247844 | 1.25 | 51 | 1.371566 | 0.783752 | 12.5 |
| 7 | 0.475125 | 0.2715 | 1.5 | 52 | 1.385214 | 0.791551 | 12.75 |
| 8 | 0.513193 | 0.293253 | 1.75 | 53 | 1.398728 | 0.799273 | 13 |
| 9 | 0.548626 | 0.313501 | 2 | 54 | 1.412114 | 0.806922 | 13.25 |
| 10 | 0.581906 | 0.332518 | 2.25 | 55 | 1.425373 | 0.814499 | 13.5 |
| 11 | 0.613383 | 0.350505 | 2.5 | 56 | 1.438511 | 0.822006 | 13.75 |
| 12 | 0.643321 | 0.367612 | 2.75 | 57 | 1.451529 | 0.829445 | 14 |
| 13 | 0.671927 | 0.383958 | 3 | 58 | 1.464432 | 0.836818 | 14.25 |
| 14 | 0.699364 | 0.399637 | 3.25 | 59 | 1.477222 | 0.844127 | 14.5 |
| 15 | 0.725765 | 0.414723 | 3.5 | 60 | 1.489902 | 0.851373 | 14.75 |
| 16 | 0.751238 | 0.429279 | 3.75 | 61 | 1.502475 | 0.858557 | 15 |
| 17 | 0.775875 | 0.443357 | 4 | 62 | 1.514944 | 0.865682 | 15.25 |
| 18 | 0.799754 | 0.457002 | 4.25 | 63 | 1.527311 | 0.872749 | 15.5 |
| 19 | 0.82294 | 0.470251 | 4.5 | 64 | 1.539579 | 0.879759 | 15.75 |
| 20 | 0.84549 | 0.483137 | 4.75 | 65 | 1.55175 | 0.886714 | 16 |
| 21 | 0.867454 | 0.495688 | 5 | 66 | 1.563826 | 0.893615 | 16.25 |
| 22 | 0.888876 | 0.507929 | 5.25 | 67 | 1.575809 | 0.900462 | 16.5 |
| 23 | 0.909794 | 0.519882 | 5.5 | 68 | 1.587702 | 0.907259 | 16.75 |
| 24 | 0.930241 | 0.531566 | 5.75 | 69 | 1.599507 | 0.914004 | 17 |
| 25 | 0.950249 | 0.542999 | 6 | 70 | 1.611225 | 0.9207 | 17.25 |
| 26 | 0.969844 | 0.554196 | 6.25 | 71 | 1.622859 | 0.927348 | 17.5 |
| 27 | 0.98905 | 0.565172 | 6.5 | 72 | 1.634409 | 0.933948 | 17.75 |
| 28 | 1.007891 | 0.575938 | 6.75 | 73 | 1.645879 | 0.940502 | 18 |
| 29 | 1.026386 | 0.586506 | 7 | 74 | 1.657269 | 0.947011 | 18.25 |
| 30 | 1.044554 | 0.596888 | 7.25 | 75 | 1.668582 | 0.953475 | 18.5 |
| 31 | 1.06241 | 0.607092 | 7.5 | 76 | 1.679818 | 0.959896 | 18.75 |
| 32 | 1.079972 | 0.617127 | 7.75 | 77 | 1.69098 | 0.966274 | 19 |
| 33 | 1.097253 | 0.627002 | 8 | 78 | 1.702069 | 0.972611 | 19.25 |
| 34 | 1.114265 | 0.636723 | 8.25 | 79 | 1.713085 | 0.978906 | 19.5 |
| 35 | 1.131022 | 0.646298 | 8.5 | 80 | 1.724032 | 0.985161 | 19.75 |
| 36 | 1.147534 | 0.655734 | 8.75 | 81 | 1.734909 | 0.991376 | 20 |
| 37 | 1.163812 | 0.665036 | 9 | 82 | 1.745718 | 0.997553 | 20.25 |
| 38 | 1.179866 | 0.674209 | 9.25 | 83 | 1.75 | 1 | 20.349 |
| 39 | 1.195703 | 0.683259 | 9.5 | Number of subzones : 82 | | | |
| 40 | 1.211334 | 0.692191 | 9.75 | Minimum zone width : 0.010810 mm | | | |
| 41 | 1.226766 | 0.701009 | 10 | Edge zone width : 0.004282 mm | | | |
| 42 | 1.242006 | 0.709718 | 10.25 | | | | |
| 43 | 1.257061 | 0.718321 | 10.5 | | | | |
| 44 | 1.271938 | 0.726822 | 10.75 | | | | |
| 45 | 1.286643 | 0.735225 | 11 | | | | |

FIG. 5

BEAM SHAPING WITHOUT INTRODUCING DIVERGENCE WITHIN A LIGHT BEAM

FIELD OF THE INVENTION

The invention relates to an optical beam shaper, particularly but not exclusively for use in an optical illumination apparatus and method. For example, optical illumination (and scanning) is used in fluorescence detection systems and methods.

BACKGROUND OF THE INVENTION

An example of the use of fluorescence detection is in nucleic acid testing (NAT). This is a core element in molecular diagnostics for detecting genetic predispositions for diseases, for determining RNA expression levels or identification of pathogens, like bacteria and viruses that cause infections.

In many cases, particularly in the identification of pathogens, the amount of target DNA present in a reasonable sample volume is very low, and this does not allow direct detection. Amplification techniques are necessary to obtain detectable quantities of the target material. Different amplification techniques have been proposed and are used in daily practice. The most widely used are based on the so-called Polymerase chain reaction (PCR).

The amplification involves the denaturing of double-stranded DNA at elevated temperature (typically >90 degrees Celsius), specific binding of primers to the DNA sample at a reduced temperature (approximately 65 degrees) and copying of the original sequences starting from the primer position (at approximately 70 degrees). This procedure is repeated and in every cycle the amount of DNA with the specific sequence is doubled (when proceeding at 100% efficiency).

After amplification, the presence of target DNA is detected by measuring the fluorescence intensity of the labeled amplified DNA, for instance after electrophoretic separation in a capillary or after hybridization to so-called capture probes which are applied in spots on a surface over which the amplification product is flowed.

The standard technique for fluorescence detection is the use of a scanning confocal microscope. Typically, a small (<1 µm), diffraction limited spot is used to excite the fluorescence in the focal plane. In the detection part of the system, only the light resulting from this single excitation point is detected.

It has previously been proposed that the excitation of a number of spots or a complete line in parallel enables an increase in the scanning speed, without a major impact on the confocality of the detection system. A pixellated detector can be used to detect the fluorescent emission. However, it has also been suggested to use a more compact detector, based on the use of a simple photodiode in combination with a slit to allow confocal detection.

In order to generate the excitation beam for a confocal line scan, it has been proposed to modify an optical device for making a scan with a focused spot by adding an optical element such as a cylinder lens, that adds so-called astigmatism. If the cross-section of a beam is defined as the xy-plane, then each ray in the beam is characterized by coordinates (x,y). The beam is astigmatic if the rays on the x-axis, coordinates (x,0) have a different focus from the rays on the y-axis, coordinates (0,y).

With the use of cylinder lenses, light which is reflected from the sample and collected by the collection lens (objective lens) will no longer be a collimated beam. The light will always be divergent in at least one direction. This may require extra effort when the light is used for auto-focus or tracking purposes.

This divergence may also arises in wide field fluorescence microscopes. In such microscopes, the excitation light is defocused to illuminate a large area of the sample.

SUMMARY OF THE INVENTION

It is inter alia an object of the invention to provide beam shaping without introducing divergence within a light beam.

The invention is defined by the independent claims. The dependent claims define advantageous embodiments.

According to the invention, there is provided an optical beam shaper. This optical beam shaper can be used to introduce astigmatism to a light beam, but can also be used to undo the astigmatism to a light beam with an orthogonal polarization state.

The optical beam shaper can comprise a diffractive element formed from birefringent material. It may, for example, comprise a plurality of zones, each zone comprising a stepped thickness defining a plurality, such as for example 4, 5, or more than 5 steps. The component can be used for introducing astigmatism to an incident collimated optical beam.

According to the invention there is further provided an optical device for illuminating a sample using the optical beam shaper.

The optical beam shaper of the invention can thus be used to defocus incoming light, so that a line focus or wide area focus can be obtained. However, the reflected light that again passes through the optical beam shaper will again be (substantially) collimated.

The optical device comprises a first detector that detects light that is reflected from the sample. This detection may serve to inspect the illumination situation on the sample with respect to focus and tracking and the like. Preferably, the optical device further comprises a controller such as for example an auto-focus system, for controlling the imaging system based on analysis of the light reflected from the sample and detected by the first detector. Thus, the reflected light can be used for a standard auto-focus and tracking method. This is particularly important when a split beam path is used. In a split beam path configuration, part of the optical path is moving with respect to the rest of the optical path during scanning. For instance the light source and the auto-focus detector are fixed, whereas the objective lens is scanned to completely interrogate the sample. This results in a variation of the distance between the objective lens and the first signal detector.

If the light between these elements is not collimated, the diameter of the beam on the signal detector will vary depending on the position of the objective lens. This will result in unwanted variations in the focus position. It is therefore important in a split beam path design to ensure that the beam between the moving parts and the fixed parts is essentially collimated.

Thus, the purpose of the polarization adjustment arrangement is to provide an orthogonal change in polarization after two passes through the arrangement. For example, the phase adjustment member comprises a quarter wave plate.

The light illuminating the sample can be arranged to comprise a line focus, for example with a width of the line being diffraction limited.

The system preferably comprises means for scanning the imaging system, and the controller then comprises a focus and tracking system. The light source (24) may comprises for example a laser diode, or a light emitting diode or any other suitable light source.

According to the invention there is provided a detection device incorporating the optical system according to the invention. The detection device comprises a second detector that is able to detect radiation generated by the illumination beam and stemming from the sample. It is amongst others this detected light that is used to gain information of the sample. The detection device benefits from all advantages of the optical system and provides improved sample inspection and a relatively less complex and costly device.

According to the invention there is also provided a method of processing a light beam an a method of illuminating a sample using the method of processing.

The illumination method may comprise a step wherein illuminating the sample comprises scanning the polarization adjusted beam across the sample and wherein controlling the imaging system comprises controlling the scanning.

BRIEF DESCRIPTION OF THE DRAWINGS

Examples of the invention will now be described in detail with reference to the accompanying drawings, in which:

FIG. 5 is a table to show one example of a calculated beam shaper configuration.

DETAILED DESCRIPTION OF EMBODIMENTS

The invention relates to the use of an optical beam shaper, for example in the form of a phase plate, that adds a phase pattern to the light beam depending on the polarization of the light beam. The plate adds a phase pattern of equal magnitude but opposite sign to two orthogonal polarization states. Furthermore, in an embodiment it is preferred that the optical beam shaper is a diffractive element with straight zones and is made of a birefringent material.

The optical beam shaper can be part of a detection device used for exciting fluorescence in a sample, for subsequent detection as part of a bio sensing procedure.

Methods are known for the detecting fluorophores in a device by exciting the fluorophores by light radiation through an objective lens and collecting the luminescence, for example through the same lens in a reflective mode. The luminescent radiation is projected onto a sensor device after having passed a filter device to select the appropriate wavelength range. The lens can be moved in a controlled way in three directions by different actuation means, to enable scanning over a sample of interest. A confocal imaging arrangement is typically used.

Figure 1:
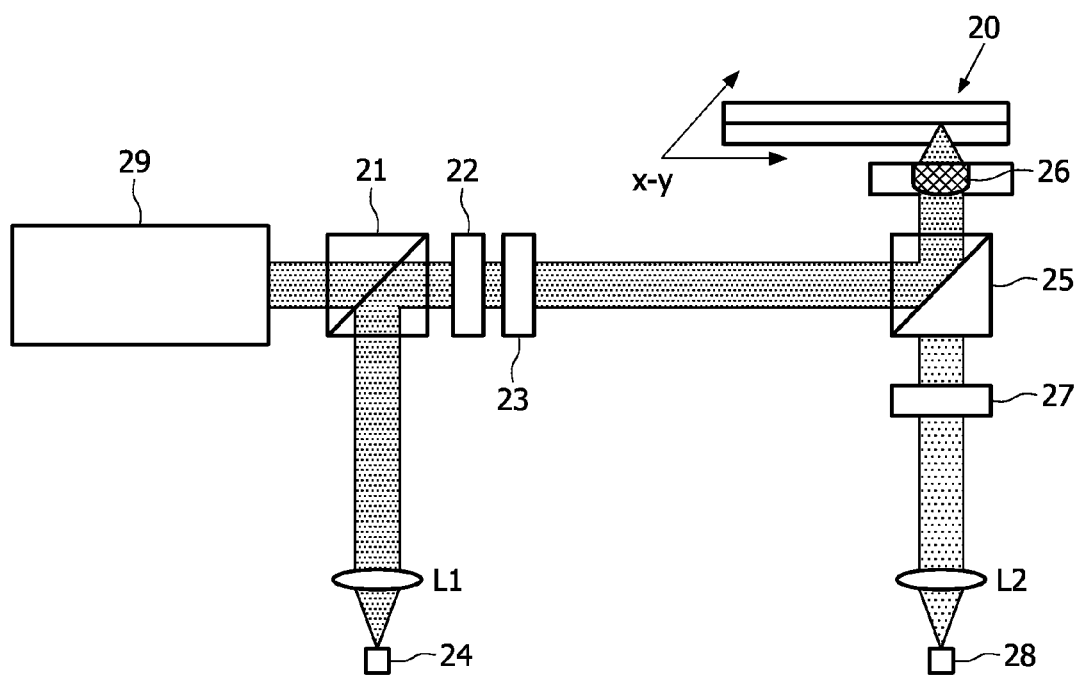
FIG. 1 shows a known fluorescence scanner.

FIG. 1 shows the basic components of a known fluorescence scanner. The sample to be investigated is confined into a given volume within a substrate 20. The light generated by a light source 24 such as a laser is used to excite fluorescence in the sample. The light emanating form the light source is collimated by a collimator lens L1. The collimated light beam is then focused in the sample by means of an excitation lens 26 after passing a polarizing beam splitter 21, a quarter wave plate 22, a band pass filter 23 and a dichroic beam splitter 25, i.e. a wavelength dependent reflector, that directs the laser light to the excitation lens 26.

The lens 26 can move relative to the sample, preferably in all three dimensions. This relative motion can be decoupled arbitrarily, for example the sample can move in to the x-y plane and the lens in the z direction. Alternatively, the sample can be kept fixed and the lens has all the three-degree of freedom (x-y-z) on its own. Any other arrangement is also possible.

The induced fluorescence, (as a result of the excitation light focused into the sample) is collected by a collection lens, which in this example is the same component as the excitation lens 26, and is directed toward a detector 28.

Any reflected unabsorbed laser light is reflected again by the beam splitter 25, whereas the fluorescence luminance is passed through the beam splitter 25. A second band pass filter 27 provides further filtering, and the light is then focused on the detector 28 by an imaging lens L2 which images the sample onto the detector.

Many different types of detector can be used such as a photon tube multiplier, avalanche photon detector, CCD detector or photodiode detector.

For confocal imaging, the excitation volume is kept to a minimum, ideally to the diffraction limited spot that the excitation lens 26 can create. A typical confocal volume is in the order of a cubic micron, depending on the strength (numerical aperture, NA) of the excitation lens 26. The fluorescence created in this volume is collected by the collection lens and is imaged on the detector. In a confocal method, the focal point is confocal with a point in the detection path. At this point in the detection path, a small pinhole is typically placed to filter out any light coming from a location other than the focal point.

The light passing the pinhole is directed toward the detector. It is possible for the detector itself to play the role of the pinhole, with the restriction that the lateral size of the detector has to match the size of the focal point scaled by the focal length of the collection lens 26 divided by the focal length of the imaging lens L2.

This confocal mode is best suited to investigate a surface immobilization assay, as the result of an endpoint bio-experiment. The surface is scanned to analyze the full sample.

The lateral dimensions of the detector are designed taking into account the fields of the collection lens 26 and the imaging lens L2.

A control arrangement 29 keeps the focus of the objective lens precisely at the inner surface of the analytical device which is in contact with the analyte, while scanning the same surface. The focus of the objective lens can also be offset on purpose.

The invention concerns in particular a modification to the system of FIG. 1 which is adapted to provide an excitation beam in the form of a confocal line, rather than a confocal spot. Alternatively, the invention can be used to defocus a light source into an excitation volume. The invention uses a polarization-dependent phase plate.

The general idea is explained with reference to FIG. 2.

Figure 2A:
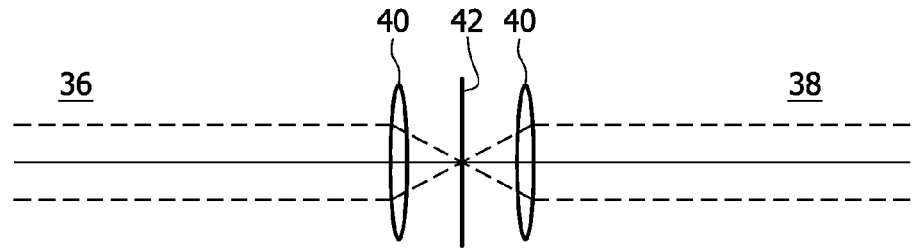
FIG. 2 schematically shows the operation of the optical system of the invention.

FIG. 2a shows the standard light path. For clarity the light path is unfolded. The incoming light 36 is focused by the focus lens 40 onto the sample 42, and the reflected light is collected by the same focus lens 40. The reflected light 38 is then completely parallel.

Figure 2B:
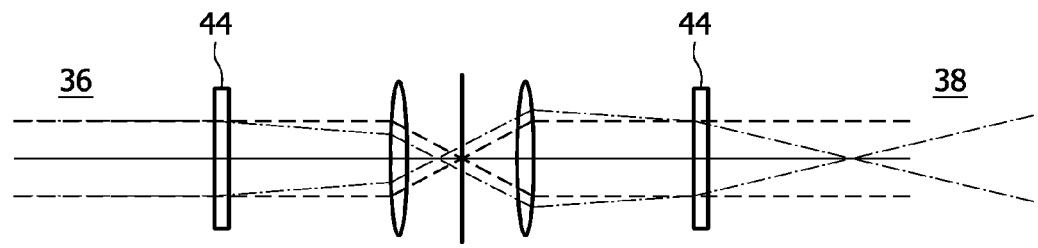

As shown in FIG. 2b, to modify the position of the focus, a refractive element 44 is placed in the incoming beam 36. When the light is now focused by lens 40 the focus will be in front of the sample 42 as shown. The reflected light will be collected by lens 40 and will pass again trough the refractive element 44. The final outgoing beam 38 will not be running parallel.

Figure 2C:
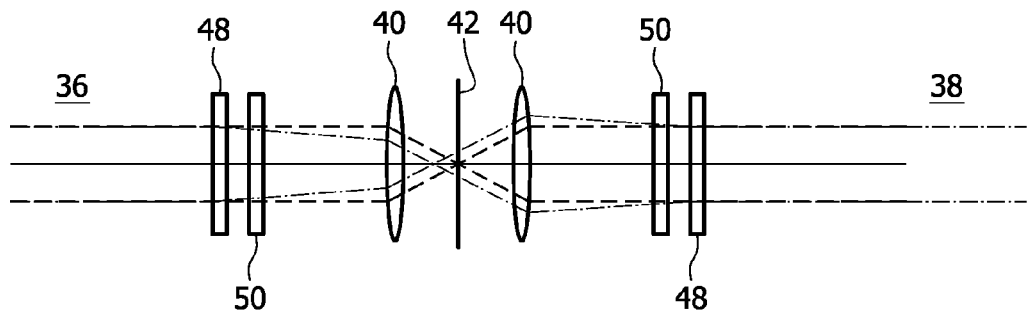

FIG. 2c shows in schematic form the optical system of the invention. The incoming beam 36 is linearly polarized, and the element 48 adds a phase pattern on the beam. This will have the same effect as that of the refractive element 44. The light passes through a quarter wave plate 50. Again, the lens 40 will focus in front of the sample 42. The reflected light is collected by lens 40 and then passes again through the quarter wave plate 50. The polarization will thus have been rotated over 90 degrees when it impinges again on element 48 and this will add a phase pattern that is opposite in sign but has the same magnitude as that was added on the incoming beam. This results in the outgoing beam 38 again being parallel.

In a preferred embodiment, the phase plate is a diffractive element made of a birefringent material, such as a photopolymerizable liquid crystal polymer, frozen in a uniaxial alignment.

An example of such a material has ordinary refractive index (for the polarization perpendicular to the alignment axis) $n_o$=1.5323 and extraordinary refractive index (for the polarization parallel to the alignment axis) $n_e$=1.6679 at wavelength λ=660 nm, giving an average refractive index n=1.6001 and a birefringence Δn=0.1356.

Figure 4:
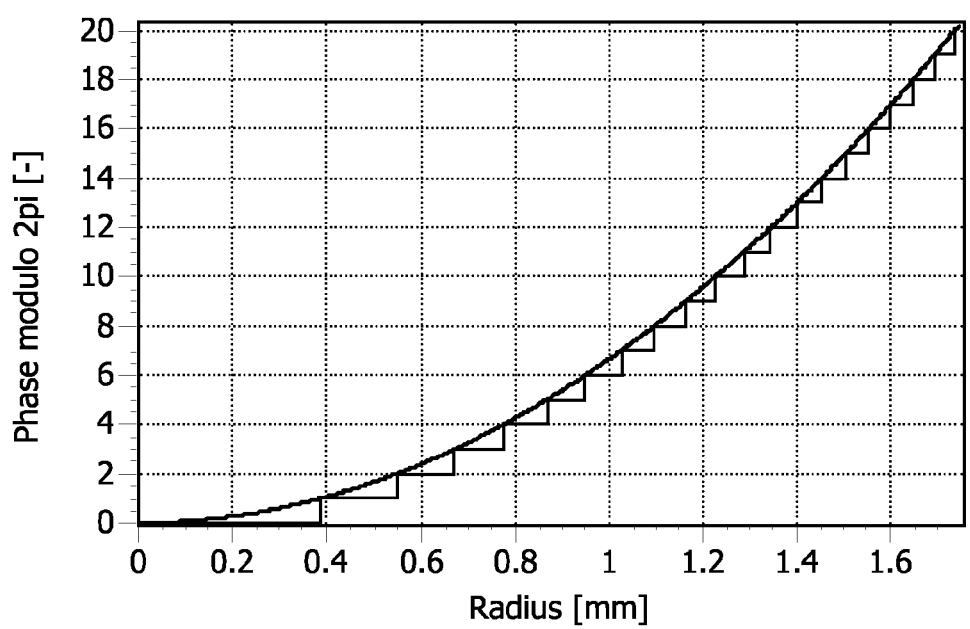
FIG. 4 shows zone positions for the optical beam shaper of FIG. 3.

The diffractive structure consists of a number of zones, each consisting of N steps, where preferably N=4 or N=5. Each step has height $h_j$ (j=0, 1, . . . , N−1) where the reference step $h_0$=0. This structure is shown in FIG. 4 in cross section. Thus, the structure is defined as a repeating set of zones, each zone having the same step height profile.

Figure 3:
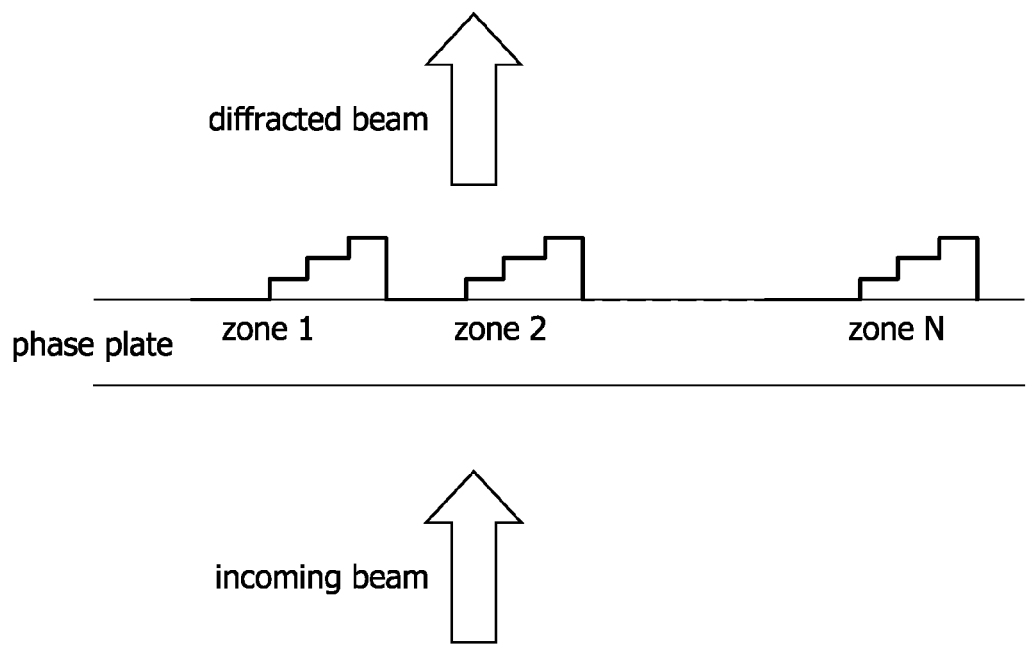
FIG. 3 shows an embodiment of an optical beam shaper according to the invention.

In FIG. 3, the diffracted beam is astigmatically aberrated depending on the polarization of the incoming beam (in the plane of the drawing or perpendicular to the plane of the drawing). The amount of astigmatism is the same in magnitude but has the opposite sign for both polarizations.

The phase for each step for the two polarization modes is then (for wavelength λ):

$$\Phi_e = \frac{2\pi(n_e - 1)h_j}{\lambda}$$

$$\Phi_o = \frac{2\pi(n_o - 1)h_j}{\lambda}$$

The phase structure splits the beam into different diffraction orders. The aim is to maximize the diffraction efficiency of the +1st (−1st) order for the e-mode and of the −1st (+1st) order for the o-mode. In that case, a phase pattern of equal magnitude but opposite sign is added to the beam for the two modes with the highest possible efficiency. The largest efficiency for an N-step grating is $[\sin(\pi/N)/(\pi/N)]^2$, which simplifies to $8/\pi^2$=81% for N=4 and $25(5-\sqrt{5})/8\pi^2$=88% for N=5. The optimum is found in case:

$$\Phi_e = 2\pi m_{e,j} + \frac{2\pi j}{N}$$

$$\Phi_o = 2\pi m_{o,j} - \frac{2\pi j}{N}$$

where $m_{o,j}$ and $m_{e,j}$ are integers. It is possible to find a set of heights $h_j$ that gives a diffraction efficiency of about 79% for both modes for N=4 and about 85% for both modes for N=5. An example of a design is given in the table below.

|  | j = 0 | j = 1 | j = 2 | j = 3 |
|---|---|---|---|---|
| $h_j$ (μm) | 0 | 2.746 | 9.353 | 7.151 |
| $\Phi_o/2\pi$ | 0 | 2.215 (2.25) | 7.543 (7.50) | 5.767 (5.75) |
| $\Phi_e/2\pi$ | 0 | 2.779 (2.75) | 9.465 (9.50) | 7.237 (7.25) |

This table gives the design of a N=4 step grating for refractive index values given for the +1st order for the o-mode and −1st order for the e-mode. The phase-values in brackets give the ideal values.

An example of a possible application is to provide a phase pattern that will add an astigmatic aberration to the beam such that when the light is focused by the objective lens, the focus will be elongated to a line with a length of around 100 μm.

The position and width of the zones and steps follows from the required astigmatic aberration function that is made. The astigmatic aberration function is:

$$W = \frac{x^2}{2f_p}$$

where x and y are the pupil coordinates, and $f_p$ is the focal length produced by the phase element. The required aberration function only depends on x, so the zones are straight stripes oriented in the y-direction. The distance between the astigmatic focal lines is then:

$$\Delta z = \frac{na^2}{NA^2 f_p}$$

where a is the pupil radius, NA the objective lens numerical aperture and n the refractive index of the medium into which is focused, and the length of the focal lines is:

$$L = 2\Delta z \frac{NA/n}{\sqrt{1 - NA^2/n^2}} = \frac{2na^2}{NA\sqrt{n^2 - NA^2}} f_p$$

For example, taking NA=0.60, n=1.33, a=1.75 mm, and a required L=100 μm, the result is $f_p$=114 mm (in this analysis the distance between the phase element and the objective lens is neglected—if this is taken into account small differences will arise).

The boundary between zone k−1 and zone k is defined by W=kλ. The width of the zone at the rim of the pupil then follows as:

$$\Delta x = \frac{\lambda f_p}{a}$$

which for the given numbers gives Δx=43 μm. For a 4-step grating this means that the smallest step width is about 11 μm. Numerically calculated step and zone boundary positions are presented in FIG. 4 and the table of FIG. 5. FIG. 4 shows the calculated zone positions for the diffractive phase element. For the parameters given, the total number of zones is 21, for a 4-step implementation this means a total number of steps of 84.

FIG. 4 shows that the zone width decreases at increasing radius from the pupil, with an initial zone width of approximately 0.4 mm and the final zone width of approximately 0.04 mm. Within each zone are the subzone steps. In FIG. 5 it can be seen that the subzone steps also decrease in width gradually. FIG. 5 shows that the second zone (subzone 5) starts at x=0.387937, corresponding to the first step shown in FIG. 5. Thus, the positions of the steps in FIG. 5 correspond to subzones 4,8,12,16, . . . etc.

The table of FIG. 5 results from calculations for a maximum diameter of 1.75 mm. The final zone is therefore altered to fit within the 1.75 mm maximum, and the expected phase of 20.5 is not reached. The value rho in the table is the normalized diameter, which extends between 0 and 1.

The height of each step above the base level of the phase plate substrate is derived from the table above.

To provide a line focus, the diffractive steps are lines in the y-direction as explained above, and the "radius" referred to in FIG. 5 is essentially a linear dimension. In this case, is the structure symmetrical about zero, i.e. the step values are the same for negative and positive values of x.

In a second example, the phase pattern can be designed to result in a circular spot with a diameter of 100 μm when the same lens as above is used (NA=0.60, n=1.33, a=1.75 mm). In this case the aberration function will depend on both x and y. The final result will be a similar step pattern as described in FIGS. 3 and 6, but the design will include a circular pattern rather than straight lines. Thus, the "radius" referred to in FIG. 5 becomes a true radius.

In a line scan method, the direction of the line in the focus plane is arranged to be perpendicular to the fast scan direction. This can be achieved by rotating the laser and beam shaper assembly.

The focus and tracking arrangement can be a standard quadrant detector, to generate the auto focus error signals. A preferred method is the astigmatic focus method as described in for instance U.S. Pat. No. 4,079,247. In this method, the reflected light is focused through an astigmatic lens (for instance a cylinder lens) onto a segmented detector with four segments. The system is aligned such that when the sample is in the ideal focus of the imaging lens, the light falls equally on all four detectors. When the sample is placed on either side of the ideal focus position, this will result in either a horizontal or vertical astigmatic line. In a standard line scan system where an astigmatic excitation beam is employed and where the reflected light is not compensated, the inherent astigmatism in the reflected beam will result will in a large offset in the focus error signal detected. This will require a complete redesign of the optical system used for autofocus purposes. By compensating the astigmatism in the reflected beam as shown in this invention no changes to the autofocus system are required.

In the example above, the lens 26 is used both for the illuminating light and the reflected light for focus and tracking, and indeed for the fluorescence illumination. However separate lenses may be used, for example with non-normal directions of illumination, or with operation in a transmissive mode.

One only detailed design for a possible polarization-dependent beam shaping element has been given. It will be apparent that the beam shaping element is designed to give rise to a desired illumination profile after the beam has passed through the lens 26. Thus, the detailed design will depend on the other optical components in the system (lens L1, lens 26, band pass filter 23) and on the birefringence of the material used to form the beam shaping element. Those skilled in the art will be able to design an appropriate beam shaping element using the techniques explained above, and the single example should not therefore be taken as limiting the scope of the invention.

The invention can be implemented as a single additional component to the system shown in FIG. 2 and inserted between the polarization beam splitter 21 and the quarter wave plate 22. However, the invention can be applied to other optical excitation/detection arrangements than the single example shown in FIG. 2.

Only one use of the component of the invention has been described above. However, the component may have other uses where it is desired to implement optical beam shaping for a first optical process, but also to undo the astigmatic effect of the beam shaping for a subsequent optical process.

Various modifications of the embodiments described herein exist. Thus, for example, the invention is described with reference to a sample that fluoresces by means of fluorophores. However, the invention may in general be used in devices that generate in a general way an optical signal. Thus samples may be measured that absorb part of the illuminating line beam so that the remaining line beam light is collected and provides a clue with respect to constitution of a sample with respect to presence, identity and/or concentration of one or more of its constituents or added substances that facilitate the constituents detection such as for example label substances. Likewise the effect of reflection of the line beam caused by the sample may be used in the detection process. Alternatively, the line beam may function as an excitation source in order to excite one/or more of the constituents of the sample or the added substances so that luminescence radiation results that can be collected and detected. Herein luminescence is meant to include fluorescence and/or phosphorescence.

In generally, the invention relates to the generation of a line for illumination of a sample. The illumination line is of advantage in a detection device as described hereinbefore. The invention is of particular interest for line scanning or confocal line scanning in order to speed up the detection process. In some cases, scanning to cover an area of a surface may however not be required. The invention will also then provide its advantages.

The invention is in general applicable in the field of sample analysis wherein samples need to be examined volumetric or on a surface. The application of the invention may thus be in analytical methods requiring line excitation. These also include analysis on gaseous, liquid and/or solid samples.

Thus the invention may be used for chemical analysis of samples such as to determine their constitution or it may be used to inspect the evolvement or progress of a chemical or biochemical or biological process. Improved scanning speed enables the collection of more data points per time unit resulting in improved dynamic measurements.

Without being limited to the field of bioanalysis, the preferred application of the invention is in the field of molecular diagnostics based on the detection of for example nucleic acids after amplification, proteins or other biochemical or biological entities. Further preferred fields of application include, clinical diagnostics, point-of-care diagnostics, advanced bio-molecular diagnostic research and optical biosensors, in particular related to DNA detection in combination with amplification methods, such as PCR, q-PCR, etc. The invention can also be used as a line scanner for imaging cells and/or tissue for example for pathology purposes. The can also be used for detection in an immunoassay to detect proteins.

The above-mentioned embodiments illustrate rather than limit the invention, and at that those skilled in the art will be able to design many alternative embodiments without departing from the scope of the appended claims. In the claims, any reference signs placed between parentheses shall not be construed as limiting the claim. The word "comprising" does not exclude the presence of elements or steps other than those listed in a claim. The word "a" or "an" preceding an element does not exclude the presence of a plurality of such elements. In the device claim enumerating several means, several of these means may be embodied by one and the same item of hardware. The mere fact that certain measures are recited in mutually different dependent claims does not indicate that the combination of these measures cannot be used to advantage.

The invention claimed is:

1. An optical system for illuminating a sample comprising:
   a light source;
   an optical beam shaper for transforming a collimated beam of light emitted by the light source into an illumination beam, the optical beam shaper comprising a polarization-dependent phase adjustment member for applying a phase pattern of equal magnitude and opposite sign to two orthogonal polarization states;
   an imaging system for illuminating the sample with the illumination beam;
   a first detector for detecting light reflected from the sample; and
   a polarization adjustment arrangement between the optical beam shaper and the sample, wherein the light reflected from the sample passes through the polarization adjustment arrangement and the optical beam shaper before detection by the first detector.

2. An optical system as claimed in claim 1, further comprising a controller for controlling the imaging system based on analysis of the light detected by the first detector.

3. A detection device, comprising:
   the optical system as claimed in claim 1;
   an optical collection arrangement for collecting light emitted from the sample and generated by the illumination beam; and
   a second detector for detecting the collected light.

4. A detection device as claimed in claim 3, wherein the imaging system and the optical collection arrangement share an excitation/collection lens.

5. An optical system as claimed in claim 1, wherein the optical beam shaper comprises a diffractive element formed from birefringent material.

6. An optical system as claimed in claim 5, wherein the diffractive element comprises a plurality of zones, each zone of the plurality of zones comprising a stepped thickness defining a plurality of steps.

7. An illumination method for illuminating a sample, comprising the steps of:
   generating a collimated light beam using a light source;
   transforming the collimated light beam into a transformed light beam by applying a phase pattern of equal magnitude and opposite sign to two orthogonal polarization states;
   passing the transformed light beam through a polarization adjustment arrangement generating an illumination light beam; and
   illuminating the sample with the illumination light beam using an imaging system.

8. An illumination method as claimed in claim 7, further comprising the steps of:
   passing a reflected light beam emanating from the illumination light beam reflected from the sample through the polarization adjustment arrangement;
   passing the re-transformed light beam to a first detector, and controlling the imaging system based on analysis of the re-transformed light beam detected by the first detector.

* * * * *